(12) United States Patent
Pons et al.

(10) Patent No.: US 9,835,506 B2
(45) Date of Patent: Dec. 5, 2017

(54) SELF-CALIBRATED FLOW METER

(71) Applicants: Institut de Radioprotection et de Sûreté Nucléaire, Fontenay-aux-Roses (FR); Universite D'Aix-Marseille, Marseilles (FR)

(72) Inventors: Serge Pons, Vinon sur Verdon (FR); Mickaël Coutin, Manosque (FR); Sébastien Luciani, Marseilles (FR); Christophe Le Niliot, Marseilles (FR); Fabrice Rigollet, Aix-en-Provence (FR)

(73) Assignees: Institut de Radioprotection et de Sûreté Nucléaire (FR); Universite D'Aix-Marseille (FR)

( * ) Notice: Subject to any disclaimer, the term of this patent is extended or adjusted under 35 U.S.C. 154(b) by 694 days.

(21) Appl. No.: 14/366,888

(22) PCT Filed: Dec. 20, 2012

(86) PCT No.: PCT/EP2012/076276
§ 371 (c)(1),
(2) Date: Jan. 15, 2015

(87) PCT Pub. No.: WO2013/092792
PCT Pub. Date: Jun. 27, 2013

(65) Prior Publication Data
US 2015/0211946 A1 Jul. 30, 2015

(30) Foreign Application Priority Data
Dec. 21, 2011 (FR) ................................ 11 62216

(51) Int. Cl.
*G01K 19/00* (2006.01)
*G01K 17/00* (2006.01)
*G01N 25/18* (2006.01)

(52) U.S. Cl.
CPC ............. *G01K 17/00* (2013.01); *G01K 19/00* (2013.01); *G01N 25/18* (2013.01)

(58) Field of Classification Search
CPC ......... G01K 19/00; G01K 17/00; G01N 25/18
See application file for complete search history.

(56) References Cited

U.S. PATENT DOCUMENTS

| 5,112,136 A | 5/1992 | Sakuma et al. | |
| 2009/0306536 A1* | 12/2009 | Ranganathan | A61B 5/01 600/549 |

(Continued)

FOREIGN PATENT DOCUMENTS

| JP | 07146189 | 6/1995 |
| JP | 2002131258 A | 5/2002 |

OTHER PUBLICATIONS

French Search Report for Application No. FR 1162216 dated Oct. 1, 2012.

(Continued)

Primary Examiner — Bryan Bui
(74) Attorney, Agent, or Firm — Lerner, David, Littenberg, Krumholz & Mentlik, LLP (57) ABSTRACT

The present invention relates to a method for estimating the thermophysical properties of a material ($\Omega$) that incorporates at least one temperature sensor (1, 2, 3) and one point heat source (4), the distance between the at least one temperature sensor (1, 2, 3) and the point heat source (4) being known. The method includes the steps of: expression of the theoretical temperature as a function of time at the at least one temperature sensor (1, 2, 3) when the point heat source (4) is activated, said expression depending on the thermophysical parameters of the material ($\Omega$); acquisition of a plurality of temperature measurements by the at least one temperature sensor (1, 2, 3) over a time period during which the point heat source (4) is activated; and determining of the values of (Continued)

the thermophysical parameters of the material ($\Omega$), such that the difference between the theoretical temperatures obtained via said expression and the temperatures that are actually measured is minimal. The present invention also relates to a method for measuring a heat flow ($\phi(t)$) across a surface ($\Gamma$) of a material ($\Omega$) and a flow meter (10) designed for this purpose.

9 Claims, 5 Drawing Sheets

(56) References Cited

U.S. PATENT DOCUMENTS

2010/0080260 A1 4/2010 Skibin et al.
2013/0306871 A1* 11/2013 Cibere ............. H01L 21/67115
250/340

OTHER PUBLICATIONS

International Search Report for Application No. PCT/EP2012/076276 dated Apr. 8, 2013.

* cited by examiner

SELF-CALIBRATED FLOW METER

CROSS REFERENCE TO RELATED APPLICATIONS

The present application is a national phase entry under 35 U.S.C. §371 of International Application No. PCT/EP2012/076276, filed Dec. 20, 2012, which claims priority from French Patent Application No. 1162216, filed Dec. 21, 2011, the disclosures of which are incorporated by reference herein.

GENERAL TECHNICAL FIELD

The present invention relates to the field of measurement of thermal transfers.

More precisely, it relates to a self-calibrated flow meter for measurement of heat flow passing through the surface of a material.

STATE OF THE ART

The thermal flow (or heat flow) $\Phi$ is defined by the power in Watts passing through a cross-section during thermal transfer. It depends on the thermophysical properties of the material wherein the heat is transmitted, especially its thermal conductivity k (also noted $\lambda$, and expressed in $W \cdot m^{-1} \cdot K^{-1}$), itself connected to the thermal diffusivity a (also noted $\alpha$, and expressed in $m^2 \cdot s^{-1}$) and to the volumetric calorific capacity $\rho C_p$ (expressed in $J \cdot m^{-3} \cdot K^{-1}$) by the expression $\alpha = \lambda / \rho C_p$.

Devices for measuring such flow, known as flow meters, are commonly employed for experimental studies in the field of materials, and more particularly to determine heat stress applied to walls subjected to a strong source of heat, typically a fire. There are many other applications, ranging from evaluation of performances of insulation of a room to detection of fire.

There are two types of flow meters mainly known and sold:
  Inertial flow meters cooled actively or by losses for direct measurement of incident flows onto a wall;
  Flow distortion flow meters for direct measurement of flow transmitted to the wall.

Inertial flow meters need to know the state of the surface and the thermophysical properties of the material, as well as their evolution over time. This requires use of a highly elaborate calibration bench and long-term operations which enable approximate flow measurements only regardless. Japanese patent JP 7146189 describes an example of such an inertial flow meter, here placed inside a wall.

Distortion flow meters comprise a flat sensor to be adhered to the wall. This sensor has the disadvantages of being intrusive (it disturbs heat flow by adding thermal resistance) and fragile (the sensors are rapidly altered or destroyed and must be replaced). Also, analysis of measurements obtained by these flow meters during different search programs has questioned their validity. They seem to derive from their calibration curve and must therefore undergo frequent recalibrating.

It would consequently be preferable to have a flow meter which is particularly reliable and which dispenses with intricate phases of calibration and recalibration.

Japanese patent application JP 2002/131258 proposes a method for resolving the heat equation enabling measurement in-situ of some thermophysical parameters which can be reused by the flow meter. It is evident however that this method does not follow the evolution of parameters over time, and that initial calibration is still necessary.

Current flow meters therefore still need to be improved.

PRESENTATION OF THE INVENTION

The aim of the present invention is to provide a heat flow meter which is capable of self-calibrating by estimating the thermophysical properties of the material tested.

For this purpose, according to a first aspect the present invention relates to a process for estimation of the thermophysical properties of a material, at least one temperature sensor and one point heat source being integrated into said material, the distance between the at least one temperature sensor and the point heat source being known, the process comprising steps of:
  expression of the theoretical temperature as a function of time at the level of the at least one temperature sensor when the point heat source is activated, said expression dependent on the thermophysical parameters of the material;
  acquisition of a plurality of temperature measurements by the at least one temperature sensor over a time period during which the point heat source is activated;
  determination of the values of the thermophysical parameters of the material such that the deviation between the theoretical temperatures obtained via said expression and the temperatures effectively measured is minimal.

According to other advantageous and non-limiting characteristics:
  said thermophysical properties of the material comprise the thermal conductivity k of the material and/or the thermal diffusivity a of the material;
  The deviation between the F theoretical temperatures obtained $\{\eta(d,t_i,\beta_1,\beta_2)\}_{i \in [1,F]}$ and the effectively measured F temperatures $\{Y(d,t_i)\}_{i \in [1,F]}$ to be minimised is expressed by the formula $$J(\beta_1, \beta_2) = \sum_{i=1}^{F} (Y(d, t_i) - \eta(d, t_i, \beta_1, \beta_2))^2,$$

d being said distance between the at least one temperature sensor and the point heat source, $\beta_1$ being a parameter inversely proportional to the thermal conductivity k, and $\beta_2$ being a parameter proportional to the thermal diffusivity a.

A second aspect of the invention relates to a process for measurement of heat flow passing through a surface of a material, at least one temperature sensor and a point heat source being integrated into said material, the distance between the at least one temperature sensor and the point heat source and the distance between the at least one temperature sensor and the surface of the material passed through by the heat flow being known, the process comprising steps of:
  Measurement over time of a plurality of internal temperatures of the material by the at least one temperature sensor;
  estimation of the thermal conductivity k and thermal diffusivity a of the material via execution of the process for estimation of the thermophysical properties of a material according to the first aspect of the invention;
  determination of the heat flow passing through the surface of the material from internal temperatures measured as a function of time by the at least one temperature sensor, the thermal conductivity k and the estimated thermal diffusivity a of the material.

According to other advantageous and non-limiting characteristics:

at least two internal temperatures are measured over time by at least two temperature sensors, one being substantially further away from the surface of the material passed through by the heat flow than the other, the process also comprising a verification step of the condition on the limits from the internal temperature measured as a function of time by the temperature sensor further away from the surface of the material.

A third aspect of the invention relates to a flow meter for measurement of heat flow passing through a surface of a material, characterised in that it comprises:

at least one temperature sensor integrated into a sample of the material;
a controllable point heat source, also integrated into the sample of the material;
means of acquisition of a plurality of temperature measurements by the at least one temperature sensor during a time interval;
processing means of the plurality of temperature measurements acquired capable of executing the process for measurement of heat flow passing through the surface of said material according to the second aspect of the invention.

According to other advantageous and non-limiting characteristics:

the flow meter comprises a first temperature sensor and a second temperature sensor, the first temperature sensor being closer to the surface of the material passed through by the heat flow than the second temperature sensor, the first temperature sensor being at a known distance from the surface of the material passed through by the heat flow, the second temperature sensor being at a known distance from the point heat source, the measurements of the first sensor being used for estimation of the heat flow, and the measurements of the second sensor being used for estimation of the thermophysical properties of the material;

the flow meter comprises a third temperature sensor, in a position relative to the known surface, the third temperature sensor being substantially further away from the surface of the material passed through by the heat flow than the first and second sensors, the measurements of the third sensor being used to understand a condition on the limits of the material;

the third temperature sensor is at a known distance from the point heat source, in particular the same as the second temperature sensor, measurements of the third sensor being compared to measurements of the second sensor to control the homogeneity of the material;

the measurements of the second sensor are also used for estimation of the heat flow when the point source is deactivated;

the temperature sensor or the temperature sensors are thermocouple and the point heat source is a heater wire, the axes of the thermocouple and the heater wire being located substantially on the same plane perpendicular to the surface of the material.

PRESENTATION OF FIGURES

Other characteristics and advantages of the present invention will emerge from the following description of a preferred embodiment. This description will be given in reference to the attached drawings, wherein.

DETAILED DESCRIPTION

General Architecture

Figure 1:
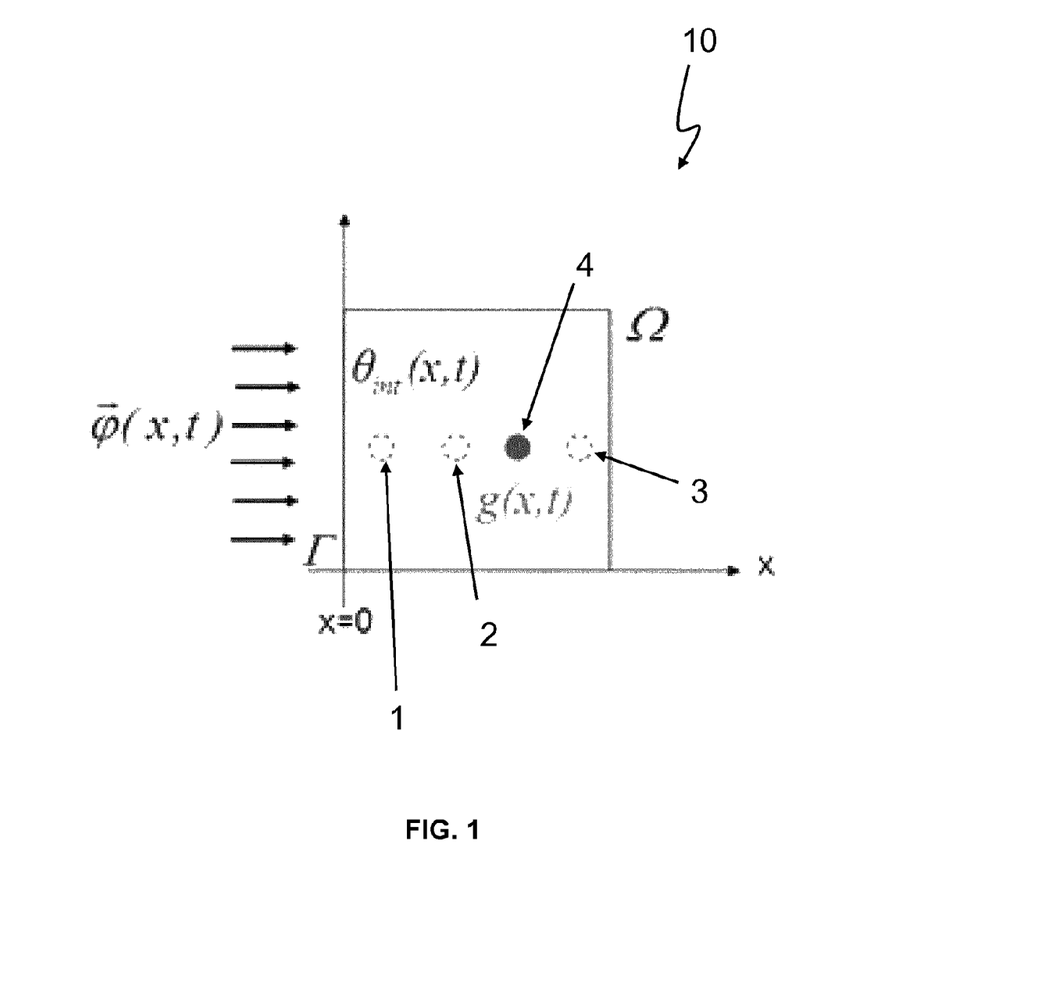
FIG. 1 is a diagram of an embodiment of a flow meter according to the invention.
Figure 2:
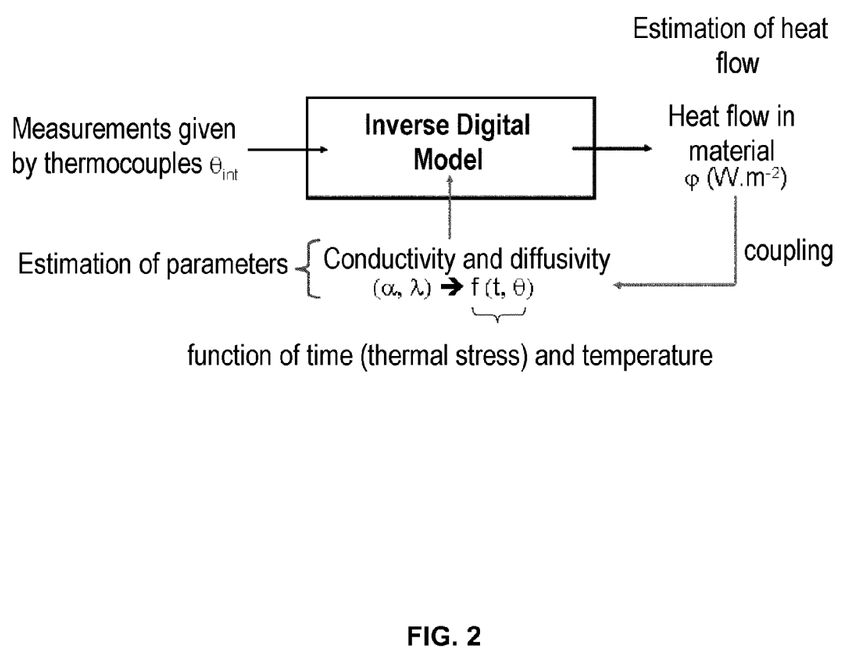
FIG. 2 diagrammatically represents the process for estimation of incoming heat flow according to the invention.

In reference to FIG. 1, the invention relates to a flow meter 10 for measurement of heat flow $\phi(t)$ passing through a surface $\Gamma$ of a material $\Omega$. It should be noted that $\phi(t)$ does not correspond to a flow in the strict sense, but to a <<density of surface flow>> at the level of $\Gamma$, i.e. $\Phi$ per surface unit, expressed in $(W \cdot m^{-2})$. The <<complete>> flow $\Phi$ which corresponds as explained to the total thermal transfer Q penetrating the material $\Omega$ per time unit, in fact gives rise to the notion of exchange surface, difficult to quantify. It is understood that the invention also relates to both measurement of flow and flow density, and the notation $\phi(t)$ will be used throughout the present description.

Also, <<passing through the surface>> of the material means both entering the material or exiting the material. In fact, even though in the majority of cases the flow is incoming (when the material is subjected to a heat source), it can be outgoing for example when the material has stored much energy and is receiving no more (intense source over a limited period). This restitution of heat means heat flow measured as negative. So, it can be necessary to make the distinction between incoming flow and outgoing flow, unless it is considered that the incoming heat flow can be positive or negative, wherein case the added precision is not an issue. Throughout the present description, an incoming flow will be considered positive for convenience.

Different possible configurations of the flow meter 10 will be described throughout the present description, but in general it comprises:

at least one temperature sensor 1, 2, 3 (advantageously two, and even more advantageously three) integrated into a sample of the material $\Omega$, which are thermocouples for example;
a controllable point heat source 4 (for example a heater wire by joule effect), also integrated into the sample of the material $\Omega$;
means of acquisition of a plurality of temperature measurements by the at least one temperature sensor during a time interval;
processing means of the plurality of acquired temperature measurements.

It should be noted that the material $\Omega$ is to be understood as invariant according to any direction orthogonal to an axis x (orthogonal to the surface $\Gamma$) according to which the flow is oriented. <<Point>> is understood as punctual, i.e. forming a point in a plane orthogonal to the surface $\Gamma$, such as the cut plane (xOz) illustrated in FIG. 1. Temperature sensors 1, 2, 3 and/or a heat source 4 extending in a direction parallel to the surface Γ (z in FIG. 1) are therefore properly <<punctual>>. If the temperature sensor or the temperature sensors 1, 2, 3 are thermocouples and the point heat source 4 is a heater wire, their axes are advantageously located substantially in the same plane perpendicular to the surface Γ of the material Ω.

The means of acquisition and processing (not illustrated) consist for example of a computer comprising a processor, a storage space, an interface for connecting the sensors 1, 2, 3 to the processor, and a man-machine interface for retrieving results.

The measurement technique is based on inverse methods, as will be shown hereinbelow. In general the two types of inverse problems, estimation of heat flow and estimation of thermophysical properties, are well separated. These inverse methods also use different digital techniques. The originality of the flow meter 10 according to the invention is in combining the two approaches in the same sample.

This technique recognises in real time the thermophysical properties to be applied to the calculation of heat flow by means of temperature measurements by the sensor or the sensors 1, 2, 3 in the material Ω exposed to the heat source.
General Principle for Estimation of Heat Flow The aim is to evaluate the heat flow φ(t) transmitted to the material by means of internal heat measurement θ at the level of a temperature sensor. To get back to this transient heat flow, an inverse problem of heat conduction must be resolved (PICC). This type of problem, known as data completion problem, belongs to the category of inverse problems for estimation of conditions on unknown limits.

The border Γ area Ω with the space variable x (one-dimensional problem) and the time variable t should be considered. The equation of the thermal system heat is expressed as:

$$\rho C_p \left( \frac{\partial \theta(x,t)}{\partial t} \right) = \vec{\nabla} \cdot \left( \lambda \vec{\nabla} \theta(x,t) \right)$$

with conditions on the limits of:
1. Condition on the surface Γ at t>0 as per Fourier's law:

$$-\lambda \left( \frac{\partial \theta(x,t)}{\partial x} \right)_{x=0} = \varphi(x=0, t) = \varphi_{surf}(t),$$

that is, simply φ(t);
2. Condition on the surface opposite Γ at t>0, or infinite medium, or known flow conditions or known temperature conditions (measurement);
3. Initial condition: $\theta(x,0) = \theta_0$ or $\theta(x,0) = f(x)$ in the field Ω at t=0.

The condition on the limits on the surface Γ is unknown here. To optimise the resolution of the equation of the heat and obtain the heat flow in real time, the aim is to produce an input-output black box system, with the internal temperature given by the sensor 1, 2, 3 $\theta_{int}(x,t)$ at entry and the heat flow density φ(t) passing through the surface Γ at exit. The aim is to express the transfer function for connecting the two magnitudes by using the theory of invariant dynamic linear systems.

In the case of an invariant linear system, the output of the system can be expressed as being the convolution of the input with the pulse response h(t) of the system plus the initial condition.

Because the thermal system is not homogeneous (the heat flow depends on the variable t), extra work has to be undertaken. To apply the theory of linear systems to the problem of heat diffusion, the Duhamel principle will be used: the solution of an initial problem to the conditions on non-homogeneous limits can be expressed as a function of the solution of the same problem with conditions on the homogeneous limits. Knowing the pulse response of the system h(t) can reveal the deduced form of the theory of linear systems.

As the impulse response of our system is given by time derivation of the step response φ(t) the Duhamel's integral is nothing else than the application of this theory to the heat equation. So if $x_1$ is the place of observation and $x_2$ the place of stress, the Duhamel principle (principle of superposition) gives:

$$\underset{\downarrow}{\text{Input}} \qquad \underset{\downarrow}{\text{Output}}$$
$$\theta_{int}(x,t) = \theta(t_0) + h(x_1,t) \otimes \varphi(x_2,t)$$

$$h(x_1, t-\tau) = -\frac{d\phi(x_1, t-\tau)}{d\tau}$$

$$\theta_{int}(x,t) = \theta_{int}(x,0) + \int_0^t \varphi(x,\tau) \cdot h(x, t-\tau) \cdot d\tau$$

$$\theta_{int}(x,t) = \theta_{int}(x,0) + \int_0^t \varphi(x,\tau) \cdot \left( -\frac{d\phi(x, t-\tau)}{d\tau} \right) d\tau$$

By discretising time by means of constant pitch, equal for integration and derivation, a matrix can be used to express Duhamel's integral and result in the following matrix system:

$$\Delta\theta = D \cdot Q$$

Δθ is the vector comprising measured internal temperatures (by one or more of the sensors 1, 2, 3 as will be shown later) minus the initial temperature, Q the vector comprising the incoming heat flow and D is a matrix created by means of the response step φ(t) of our thermal system.

This method offers excellent results. The person skilled in the art can however employ other methods for calculating flow as a function of the temperature measurements and the thermophysical parameters of the material.
Process for Estimation of Thermophysical Properties According to a first aspect, the invention relates to a process for estimation of the thermophysical properties of a material Ω, by way of which calculate the missing step response in the preceding calculation. These thermophysical properties advantageously comprise the thermal conductivity k of the material Ω and/or the thermal diffusivity a of the material Ω. The invention is not limited to these parameters, and could for example comprise estimation of ρCp.

This process utilises the point heat source 4 integrated into the material Ω, where the distance between the at least one temperature sensor 1, 2, 3 and the point heat source 4 must be known. Given that the heat source is controlled, it is known how to express the temperatures expected to be measured as a function of the preferred thermophysical parameters.

The process comprises steps of:
expression of the theoretical temperature as a function of time at the level of the at least one temperature sensor 1, 2, 3 when the point heat source 4 is activated, said expression dependent on the thermophysical parameters of the material Ω;

acquisition of a plurality of temperature measurements by the at least one temperature sensor 1, 2, 3 during a time interval during which the point heat source 4 is activated;

determination of the values of the thermophysical parameters of the material Ω such that the deviation between the theoretical temperatures obtained via said expression and the temperatures effectively measured is minimal.

The temperature θ is measured at the instant t by a sensor 1, 2, 3 placed at a distance d from the heat source 4. This heater wire is subjected to an echelon of constant linear heat flow g (W·m$^{-1}$) and is supposed to be in an infinite medium, as is the case for short times t ($t_{experience}$<300 s). The rise in theoretical temperature is given in particular by the equation:

$$\eta(t) = \theta(t) - \theta_0 = \frac{-g}{4\pi k} E_I\left(\frac{-d^2}{4at}\right) \text{ with } -E_I(-x) = \int_x^{+\infty} \frac{e^{-u}}{u} du$$

In this equation, deduced from the heat equation, $\theta_0$ is the initial temperature in Kelvins, k the thermal conductivity in W·m$^{-1}$·K$^{-1}$, a the diffusivity in m$^2$·s$^{-1}$, g the linear power of the source 4 in W·m$^{-1}$ and $E_I$ is the integral exponential function.

Noting that the expression of the theoretical temperature reveals two independent parameters whereof one is a parameter $\beta_1$ inversely proportional to the thermal conductivity k, and $\beta_2$ a parameter proportional to the thermal diffusivity a $$\left(\beta_1 = \frac{g}{4\pi k} et \ \beta_2 = \frac{a}{d^2}\right),$$

the deviation between the F theoretical temperatures obtained by this formula (noted $\{\eta,d,t_i,\beta_1,\beta_2)\}_{i\in[1,F]}$) and the effectively measured F temperatures $\{Y(d,t_i)=\theta_{int}(d,t)-\theta_0\}_{i\in[1,F]}$ to be minimised is a quadratic deviation expressed by the formula $$J(\beta_1, \beta_2) = \sum_{i=1}^{F} (Y(d, t_i) - \eta(d, t_i, \beta_1, \beta_2))^2.$$

The F points of comparison are taken at different instants $t_i$ (i=1 to F) of the signal. The best estimations of the parameters (noted <<^>>) are such that:

$$(\hat{\beta}_1, \hat{\beta}_2) = \text{arguments}\{\text{minimum}(J(\beta_1, \beta_2))\}$$

This is therefore an estimation of the type 'ordinary least squares'. The feasibility of simultaneous estimation of the two parameters has been demonstrated by prior sensitivity analysis which has shown that each parameter had a sufficiently large and independent influence on the model.

The estimations $\hat{\beta}_1$ and $\hat{\beta}_2$ allow to deduce the preferred values of conductivity k and diffusivity a, as well as their confidence interval.

Estimation of the uncertainty of the estimated parameters is done according to the method of sensitivities. If the measurement noise is random, constant Gaussian centre of standard deviation σ, the matrix of variance-covariance of the estimated parameters can be determined. If the matrix of sensitivities to the parameters is noted as X, this gives:

$$\begin{bmatrix} \sigma_{\hat{\beta}_1}^2 & \text{cov}(\hat{\beta}_1, \hat{\beta}_1) \\ \text{cov}(\hat{\beta}_1, \hat{\beta}_1) & \sigma_{\hat{\beta}_1}^2 \end{bmatrix} = \sigma^2 (X^T X)^{-1}$$

The resulting standard deviation is similar to the uncertainty u(b) on the parameter b. This could be uncertainty of type A, the latter resulting from a statistical calculation. In our case, the uncertainty composed is calculated such as:

$$\frac{u(k)}{k} = \sqrt{\left(\frac{u(g)}{g}\right)^2 + \left(\frac{u(\beta_1)}{\beta_1}\right)^2}$$

$$\frac{u(a)}{a} = \sqrt{2\left(\frac{u(d)}{d}\right)^2 + \left(\frac{u(\beta_2)}{\beta_2}\right)^2}$$

For a precise estimation the following must be known and controlled in the least uncertainly possible way:

The distance from the source 4 to the sensor 1, 2, 3 (to be controlled at manufacture, fixed after);

The uniformity of the source 4 of linear heat g=> homogeneous material, of constant diameter, not hardened so as to have perfectly homogeneous resistance along the wire (linear resistance). The diameter of the wire must be comparable to that of the thermocouple (inertia).

Example of Estimation of Thermophysical Parameters

Figure 3A:
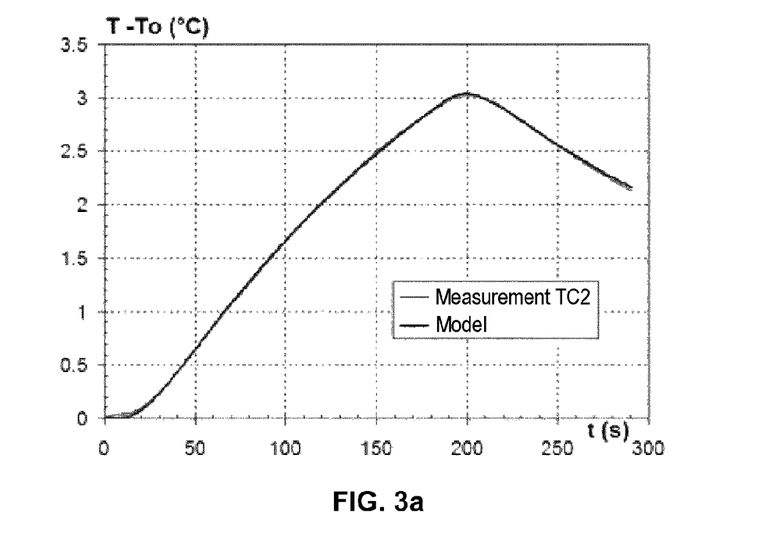
FIGS. 3a and 3b are two graphics obtained from a test of the process for estimation of the thermophysical parameters of a material according to the invention, representing respectively the theoretical and measured temperatures over a given time interval, and their deviation over the same time interval.

FIG. 3a shows in the same theoretical graphic θ–$\theta_0$ measured as a function of time. The two curves are quasi superposed.

Figure 3B:
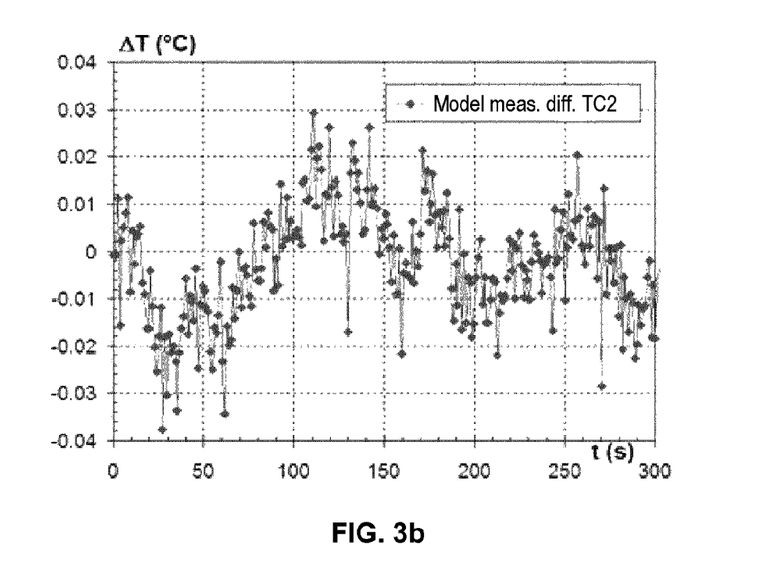

The deviation (η–Y) for the optimal parameters $\beta_1$ and $\beta_2$ is illustrated in FIG. 3b. As is evident, this deviation never exceeds 0.04° C. in absolute value. Uncertainty of the identified parameters (see hereinbelow) is therefore particularly low.

| Parameters | Values |
| --- | --- |
| $\beta_1$ | 2.36825962 |
| $\beta_2$ | 0.004711 |
| Residue (° C.$^2$) | 0.033135 |
| Average (° C.) | −0.0022 |
| Standard deviation (° C.) | 0.0118 |
| d (mm) | 10 |
| a (m$^2$ · s$^{-1}$) | 4.7112$^E$−07 |
| k (W · m$^{-1}$ · K$^{-1}$) | 0.884 |

$k = \frac{g}{4\pi\beta_1} \quad a = d^2\beta_2$ k = 0.88 ± 0.08 Wm$^{-1}$ · ° C$^{-1}$ a = (4.7 ± 0.1) × 10$^{-7}$ m$^2$ · s$^{-1}$ Process for Measurement of Heat Flow According to a second aspect, the invention relates to a process for measurement of heat flow φ(t) passing through a surface Γ of the material Ω wherein the previously estimated thermophysical parameters are used.

The distance between the at least one temperature sensor 1, 2, 3 and the surface Γ of the material Ω passed through by the heat flow must be known.

The process comprises steps of:

measurement over time of a plurality of internal temperatures of the material Ω by the at least one temperature sensor 1, 2, 3, estimation of the thermal conductivity k and of the thermal diffusivity a of the material Ω by execution of the process for estimation of the previously explained thermophysical properties of material $\Omega$;

determination of the heat flow $\phi(t)$ passing through the surface $\Gamma$ of the material $\Omega$ from the internal temperatures measured as a function of time by the at least one temperature sensor 1, 2, 3, of the thermal conductivity k and of the thermal diffusivity a estimated of the material $\Omega$.

The coupling measurement of heat flow/estimation of the thermophysical properties can be taken during an assay. A power peak during a given time is generated in the heater wire 4 over a period when the heat flow transmitted to the material is constant. The new conductivities and diffusivities are estimated by means of the principle of superposition. In practice, the component due to heat flow is removed from the signal so as to retain only perturbation due to the heater wire. The new thermophysical parameters are then reinjected into the inversion algorithm of the temperature for calculation of the flow such as described previously.

To estimate the heat flow passing through the surface $\Gamma$ of the material $\Omega$, the procedure consists advantageously of searching in a database for the step response for each conductivity and diffusivity couple as function of the internal temperature of the temperature sensor, and inverting them to resolve the formula $\Delta\theta = D \cdot Q$ mentioned previously. It is also possible to recalculate this response each time the process is run.

Verification of Conditions on Fixed Limits

The model used supposes that a condition called <<semi-infinite>> medium is verified, in terms other than the material $\Omega$ occupies all of the demi-space located to one side of the surface $\Gamma$ (in this case $\{(x,y,z) \in \mathbb{R}^3, x \geq 0\}$). In reality, the material is limited by its rear face, and the condition of semi-infinite medium can no longer be respected.

Advantageously, at least two internal temperatures are measured over time by at least two temperature sensors, one 3 being substantially further away from the surface $\Gamma$ of the material $\Omega$ passed through by the heat flow $\phi(t)$ than the other (1, in reference to FIG. 1), the process also comprising a verification step of the condition on the limits from the internal temperature measured as a function of time by the temperature sensor 3 further away from the surface $\Gamma$ of the material $\Omega$.

A plurality of embodiment of the flow meter 10 according to the invention will now be described, as a function of the number of temperature sensors it comprises.

First Embodiment of the Flow Meter: One Temperature Sensor

The flow meter 10 can comprise just one temperature sensor. In this case, it is the sensor 1 of FIG. 1. The latter must be at a known distance both from the surface $\Gamma$ and the point source 4. This embodiment produces a highly compact and barely invasive flow meter. It is however limited as it cannot both measure heat flow $\phi(t)$ and estimate the thermophysical properties of the material $\Omega$. The flow is measured in fact during phases during which the source 4 is off (deactivated), whereas estimation of the properties needs this source 4 to be on (activated). This is done during stationary phases during which heat flow transmitted to the material is constant.

Second Embodiment of the Flow Meter: Two Temperature Sensors

More advantageously, the flow meter 10 comprises a first temperature sensor 1 and a second temperature sensor (sensor 2 or 3 of FIG. 1), the first temperature sensor 1 being closer to the surface of the material $\Omega$ passed through by the heat flow $\phi(t)$ than the second temperature sensor 2, 3.

In this case, it is the first temperature sensor 1 which is at a known distance from the surface $\Gamma$ of the material $\Omega$ passed through by the heat flow $\phi(t)$, whereas it is the second temperature sensor 2, 3 which is at a known distance from the point heat source 4. The two sensors are advantageously relatively distant to be the most independent possible.

The first sensor 1 is dedicated to measurement of the heat flow $\phi(t)$ since it is that which is closer to the surface. The second sensor 2, 3 is as such dedicated to estimation of the thermophysical properties of the material $\Omega$. Each sensor can take measurements independently of the other, and the coupling measurement of heat flow/estimation of the thermophysical properties can be taken in real time. In practice, the component due to heat flow can be taken from measurement of the second sensor 2, 3 so as to retain only the perturbation due to the source 4, and reciprocally the component due to the heat source 4 can be taken from measurement of the first sensor 1 when it is active so as to retain only perturbation due to the heat flow.

However, particularly preferably, the measurements of the second sensor 2, 3 are also used for estimation of the heat flow $\phi(t)$ when the point source 4 is deactivated. With two sensors, to a large extent imprecision due for example to imperfections of the material $\Omega$ are eliminated.

Third Embodiment of the Flow Meter: Three Temperature Sensors

Even more advantageously, the flow meter 10 is as per FIG. 1: it comprises a third temperature sensor 3. As explained previously, the latter is substantially further away from the surface $\Gamma$ of the material $\Omega$ passed through by the heat flow $\phi(t)$ than the first and second sensors 1 and 2. The measurements of the third sensor 3 are used to understand a condition on the limits of the material F.

The third temperature sensor 3 is advantageously a <<second>> second sensor: on condition it is at a known distance from the point heat source 4 (in particular the same as the second temperature sensor 2, for easier calculations), measurements of the third sensor 3 can be compared to measurements of the second sensor 2 to confirm the estimations of thermophysical parameters and control the homogeneity of the material $\Gamma$.

It should be noted that the flow meter 10 can comprise more than three temperature sensors: a plurality of <<first>> sensors 1, and/or a plurality of <<second>> sensors 2, and/or a plurality of <<third>> sensors 3 is feasible.

Example of Measurement of Heat Flow

Figure 4:
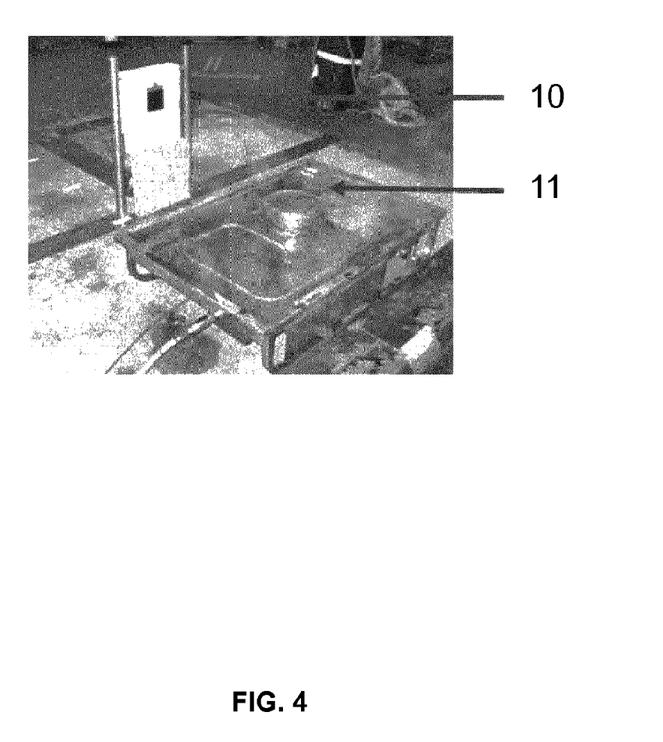
FIG. 4 represents an example of installation for testing the process for estimation of incoming heat flow in a material.

The invention has been tested on specific qualification assays using two types of heat source (homogeneous and non-homogeneous):

homogeneous source (the surface of the flow meter is in contact with heating resistance or exposed before a black body);

non-homogeneous source (the surface of the flow meter is exposed for example to a flame of a gas burner 11, in reference to FIG. 4).

Figure 5A:
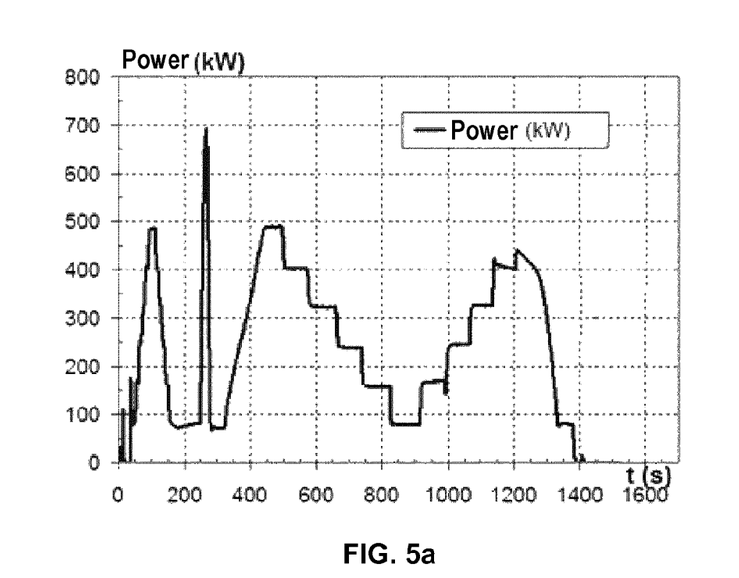
FIGS. 5a and 5b are two graphics obtained from a test of the process for estimation of incoming heat flow in a material according to the invention, representing respectively the thermal power to which the material has been subjected as a function of time, and the incoming heat flow in the resulting material.
Figure 5B:
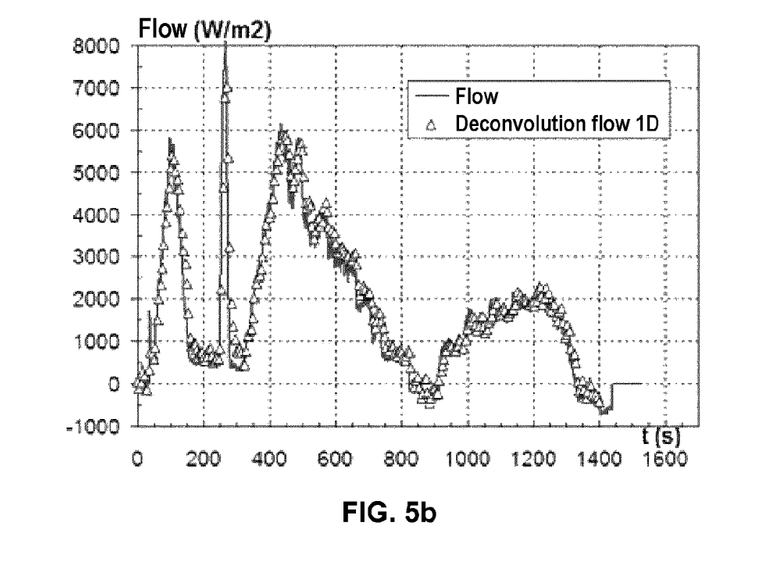

FIG. 5a has the thermal power profile to which the material $\Omega$ equipped with the flow meter 10 according to the invention is subjected, during a qualification test with the gas burner 11. The power of the fire is controlled by variation in the rate of injected gas. The flow meter 11 has estimated the heat flow $\Phi$ (this is the surface flow $\phi_{surf}(t)$ which is illustrated in FIG. 5b) passing through the surface Γ of the material Ω, and has characterised the conductivity k and the diffusivity a of the material Ω by means of the heating source 4. The coupling implemented by the invention enables better estimation of the heat flow as it takes into account the evolution of the properties. This evolution can be characterised between each assay (stationary operation) to take into account the ageing of the material or to take into account the evolution of the thermophysical properties as a function of temperature during use.

Applications

Since it is robust, integrated in-situ into the material and has a controlled metrological process, the flow meter 10 according to the invention can be used in many fields:
- for themes linked or not to fire and for searches on the medium/wall interaction in a thermally and chemically aggressive environment;
- for direct measurements of heat flow or for follow-up of the evolution of heat flow over long periods (application to thermal ageing of materials on extended time scales).

Also, it can be used as a building standard. The thermocouple and the heater wire implanted in the walls of the construction materials can serve to:
- set up a precise energy balance of a building especially to evaluate its class of insulation;
- set up an energy balance in real time so as to implement the regulations necessary for maintaining a comfortable temperature;
- over time follow degradation of the thermal properties of the walls: desiccation, water infiltration, degradation of existing insulation;
- determine the thermodynamic state of premises on fire equipped with this flow meter (pre-flashover, flashover, post-flashover) enabling crisis management by firefighting units in case of fire;
- detect fire in the same way as other safety measures such as smoke detectors.

The invention claimed is:

1. A process for estimation of the thermophysical properties of material (Ω), at least one temperature sensor and one point heat source being integrated into said material (Ω), the distance between the at least one temperature sensor and the point heat source being known, the process comprising steps of:
- expression of the theoretical temperature as a function of time at the level of the at least one temperature sensor when the point heat source is activated, said expression dependent on the thermophysical parameters of the material (Ω);
- acquisition of a plurality of temperature measurements by the at least one temperature sensor during a time interval during which the point heat source is activated;
- determination of the values of the thermophysical parameters of the material (Ω) such that the deviation between the theoretical temperatures obtained via said expression and the temperatures effectively measured is minimal;
- wherein said thermophysical properties of the material (Ω) comprise the thermal conductivity k of the material (Ω);
  - wherein the deviation between the F theoretical temperatures obtained $\{\eta(d,t_i,\beta_1,\beta_2)\}_{i\in[1,F]}$ and the effectively measured F temperatures $\{Y(d,t_i)\}_{i\in[1,F]}$ to be minimised is expressed by the formula $$J(\beta_1, \beta_2) = \sum_{i=1}^{F} (Y(d, t_i) - \eta(d, t_i, \beta_1, \beta_2))^2,$$

d being said distance between the at least one temperature sensor and the point heat source, $\beta_1$ being a parameter inversely proportional to the thermal conductivity k, and $\beta_2$ being a parameter proportional to the thermal diffusivity a.

2. A measurement process of heat flow ($\phi(t)$) passing through a surface (Γ) of a material (Ω), at least one temperature sensor and one point heat source being integrated into said material, the distance between the at least one temperature sensor and the point heat source and the distance between the at least one temperature sensor and the surface (Γ) of the material (Ω) passed through by the heat flow ($\phi(t)$) being known, the process comprising steps of:
- measurement over time of a plurality of internal temperatures of the material (Ω) by the at least one temperature sensor;
- estimation of the thermal conductivity k and of the thermal diffusivity a of the material (Ω) by the execution of the process for estimation of the thermophysical properties of a material (Ω), according to claim 1;
- determination of the heat flow ($\phi(t)$) passing through the surface (Γ) of the material (Ω) from the internal temperatures measured as a function of time by the at least one temperature sensor, of the estimated thermal conductivity k and the thermal diffusivity a of the material (Ω).

3. The process according to claim 2, at least two internal temperatures are measured over time by at least two temperature sensors, one being substantially further away from the surface (Γ) of the material (Ω) passed through by the heat flow ($\phi(t)$) than the other, the process also comprising a verification step of the condition on the limits from the internal temperature measured as a function of time by the temperature sensor further away from the surface (Γ) of the material (Ω).

4. A flow meter for measurement of heat flow ($\phi(t)$) passing through a surface (Γ) of a material (Ω) wherein it comprises:
- at least one temperature sensor integrated into a sample of the material (Ω);
- a controllable point heat source, also integrated into the sample of the material (Ω);
- means of acquisition of a plurality of temperature measurements by the at least one temperature sensor during a time interval;
- processing means of the plurality of acquired temperature measurements capable of executing the process for measurement of heat flow ($\phi(t)$) passing through the surface (Γ) of said material (Ω), according to claim 2.

5. The flow meter according to claim 4, comprising a first temperature sensor and a second temperature sensor, the first temperature sensor being closer to the surface (Γ) of the material (Ω) passed through by the heat flow ($\phi(t)$) than the second temperature sensor, the first temperature sensor being at a known distance from the surface (Γ) of the material (Ω) passed through by the heat flow ($\phi(t)$), the second temperature sensor being at a known distance from the point heat source, the measurements of the first sensor being used for estimation of the heat flow ($\phi(t)$), and the measurements of the second sensor being used for estimation of the thermophysical properties of the material (Ω).

6. The flow meter according to claim 5, comprising a third temperature sensor, of position relative to the known surface, the third temperature sensor being substantially further away from the surface ($\Gamma$) of the material ($\Omega$) passed through by the heat flow ($\phi(t)$) than the first and second sensors, the measurements of the third sensor being used to understand a condition on the limits of the material ($\Omega$).

7. The flow meter according to claim 6, wherein the third temperature sensor is at a known distance from the point heat source, in particular the same as the second temperature sensor, measurements of the third sensor being compared to measurements of the second sensor to control the homogeneity of the material ($\Gamma$).

8. The flow meter according to claim 5, wherein the measurements of the second sensor are also used for estimation of the heat flow ($\phi(t)$) when the point source is deactivated.

9. The flow meter according to claim 4, wherein the temperature sensor or temperature sensors are thermocouples and the point heat source is a heater wire, the axes of the thermocouple and the heater wire being located substantially in the same plane perpendicular to the surface ($\Gamma$) of the material ($\Omega$).

\* \* \* \* \*